(12) United States Patent
Landwehr

(10) Patent No.: US 9,962,509 B2
(45) Date of Patent: May 8, 2018

(54) PROCESS AND DEVICE FOR GENERATING AN ALARM DURING A MACHINE-ASSISTED PATIENT VENTILATION

(71) Applicant: Dräger Medical GmbH, Lübeck (DE)

(72) Inventor: Birger Landwehr, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 532 days.

(21) Appl. No.: 14/644,615

(22) Filed: Mar. 11, 2015

(65) Prior Publication Data

US 2015/0258290 A1    Sep. 17, 2015

(30) Foreign Application Priority Data

Mar. 12, 2014  (DE) .................. 10 2014 003 542

(51) Int. Cl.
*A61M 16/00* (2006.01)
*A61B 5/00* (2006.01)
*A61B 5/091* (2006.01)
*G06F 19/00* (2018.01)

(52) U.S. Cl.
CPC ......... *A61M 16/0051* (2013.01); *A61B 5/091* (2013.01); *A61B 5/4836* (2013.01); *A61B 5/746* (2013.01); *A61M 16/021* (2017.08); *G06F 19/3406* (2013.01); *A61M 16/024* (2017.08); *A61M 2016/0033* (2013.01); *A61M 2205/18* (2013.01); *A61M 2205/3386* (2013.01)

(58) Field of Classification Search
None
See application file for complete search history.

(56) References Cited

U.S. PATENT DOCUMENTS

| | | | | |
|---|---|---|---|---|
| 6,731,984 B2* | 5/2004 | Cho | ................... | A61N 1/36542 607/17 |
| 7,361,146 B1* | 4/2008 | Bharmi | .............. | A61B 5/02405 600/481 |
| 2002/0193839 A1 | 12/2002 | Cho et al. | | |

(Continued)

FOREIGN PATENT DOCUMENTS

| | | |
|---|---|---|
| CN | 101422366 A | 5/2009 |
| CN | 101563028 A | 10/2009 |

(Continued)

*Primary Examiner* — Tan-Uyen (Jackie) T Ho
*Assistant Examiner* — Joseph D Boecker
(74) *Attorney, Agent, or Firm* — McGlew and Tuttle, P.C.

(57) ABSTRACT

A device and process generates an alarm during a machine-assisted ventilation of a patient. A minute volume is measured and a median of the minute volume and a lower critical limit value of the minute volume and a time delay are determined and are recorded in a control device. A reference signal is determined as a function of the lower critical limit value for the minute volume and the time delay based on the median of the minute volume. From the reference signal an alarm limit value located below the lower critical limit value as well as a value for a maximum tolerated duration of apnea of the patient are derivable. An alarm signal is generated both during an undershooting of the lower critical limit value over a period of time that is longer than the established time delay and during an undershooting of the alarm limit value.

27 Claims, 11 Drawing Sheets

(56) References Cited

U.S. PATENT DOCUMENTS

| | | | |
|---|---|---|---|
| 2004/0249299 A1* | 12/2004 | Cobb | A61B 5/0205 600/529 |
| 2005/0061320 A1* | 3/2005 | Lee | A61M 16/00 128/204.18 |
| 2005/0119586 A1* | 6/2005 | Coyle | A61B 5/0806 600/538 |
| 2007/0221224 A1* | 9/2007 | Pittman | A61M 16/0051 128/204.22 |
| 2009/0050155 A1* | 2/2009 | Alder | A61B 5/087 128/204.23 |
| 2009/0234240 A1 | 9/2009 | Kuenzler et al. | |
| 2010/0016682 A1 | 1/2010 | Schluess et al. | |
| 2010/0307500 A1* | 12/2010 | Armitstead | A61B 5/087 128/204.23 |
| 2011/0040201 A1 | 2/2011 | Pu et al. | |
| 2011/0068929 A1 | 3/2011 | Franz et al. | |
| 2015/0165145 A1 | 6/2015 | Alder et al. | |

FOREIGN PATENT DOCUMENTS

| | | |
|---|---|---|
| CN | 102526850 A | 7/2012 |
| EP | 2 302 606 B1 | 6/2013 |
| WO | 2013/177621 A1 | 12/2013 |

\* cited by examiner

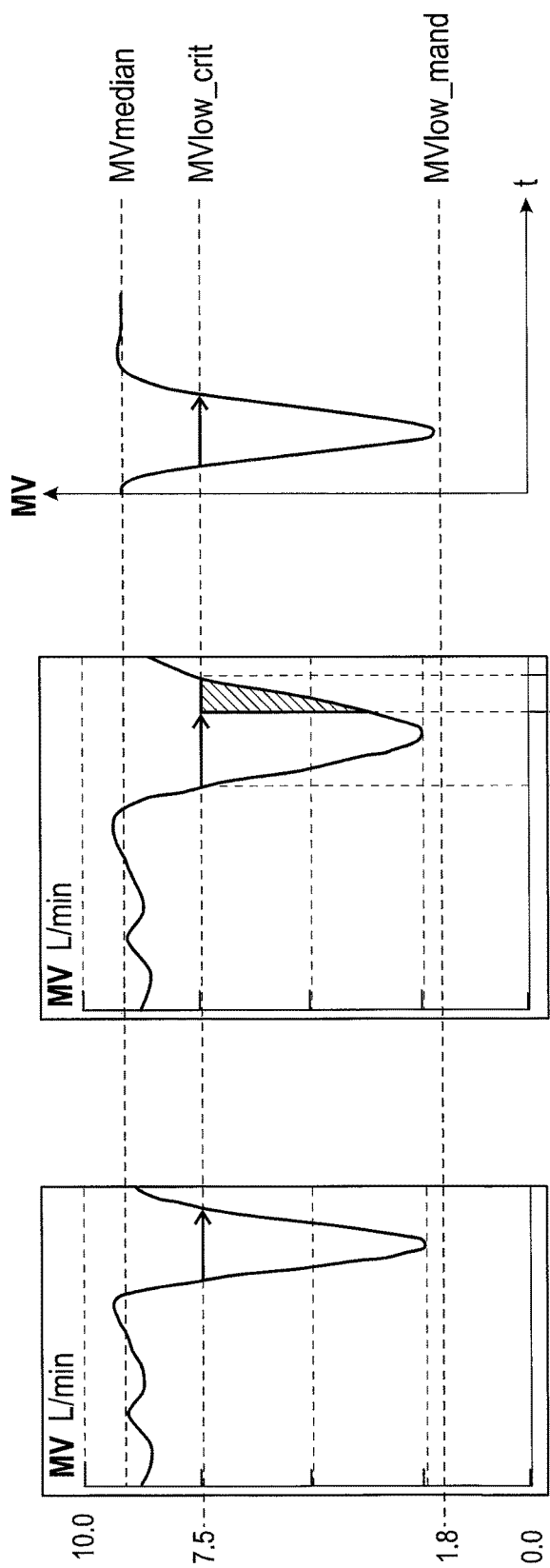

PROCESS AND DEVICE FOR GENERATING AN ALARM DURING A MACHINE-ASSISTED PATIENT VENTILATION

CROSS REFERENCE TO RELATED APPLICATIONS

This application claims the benefit of priority under 35 U.S.C. § 119 of German Patent Application DE 10 2014 003542.5 filed Mar. 12, 2014, the entire contents of which are incorporated herein by reference.

FIELD OF THE INVENTION

The present invention pertains to a process as well as a device for generating an alarm during a machine-assisted ventilation (also known as respiration) of a patient for generating an alarm during a machine-assisted ventilation of a patient, in which a minute volume is measured and a median of the minute volume is determined as well as a lower critical limit value of the minute volume and a time delay, with which the sending of an alarm after undershooting the lower critical limit value is generated, are recorded in a control device. Further, the present invention pertains to a control device as well as software implemented in a control device for implementing the process.

BACKGROUND OF THE INVENTION

In many cases, an artificial ventilation is necessary in the treatment of a patient, for example, in the area of intensive care, in surgeries or in emergency situations. Depending on the application in this case, external devices take over the respiration of a patient entirely or assist it. Thus, for example, respirators without rebreathing are used for the artificial ventilation of patients on intensive care units in hospital, while in anesthesia devices with closed system, the exhalation gas exhaled by the patient is reused as inhalation gas. The technical solution described in detail below for generating an alarm can be used both for correspondingly designed ventilators (also known as respirators) and for anesthesia devices.

Avoiding clinically irrelevant alarms has great importance in today's medical devices. While for a long time the focus in the development of alarm-capable monitoring devices was placed on the clear and early recognition and alerting of dangerous situations in the monitoring of a patient, nowadays reduction in the number of alarms to a clinically necessary minimum is more and more the focus. This can, above all, be attributed to the fact that more and more alarm-capable devices, for example, syringe pumps, monitors and respirators, are arranged in the area of the patient. Thus, the health care staff as well as the patients are exposed to a high acoustic discomfort and the risks resulting from this are among the highest that are currently connected with medical devices. Based on the problem described, nowadays a principal aspect in the development of medical devices subject to alarm lies in optimizing the alarm frequency to the effect that, on the one hand, dangerous situations are always clearly recognized and, on the other hand, irrelevant alarms are largely suppressed. In this way, an insidious desensitization of the health care staff because of the many alarms shall be prevented in spite of maintaining a high safety standard.

A process for alarm generation in alarm-capable medical devices is known from EP 2 302 606 B1. The process described is essentially based on the fact that, in addition to establishing relevant limit values, a so-called verification interval is recorded, whereby an alarm is only triggered if a preset limit value is undershot or overshot over the entire duration of the verification interval. In each case, the recorded verification interval has a time-limited verification interval length, which usually decreases with increasing degree of danger of the patient. The delay interval length defined for the lowest degree of danger thus corresponds to the maximum possible alarm delay of a slight over- or undershooting of the corresponding limit value, while an alarm is very quickly triggered in case of sharp deviations of a recorded measured value from the limit value. The establishing of a danger potential is thus essential to the technical solution described.

In order to be able to optimally estimate possible dangerous situations in an artificial ventilation of a patient, it is necessary to consider additional characteristics, for example, a breathing disorder that is present during the monitoring of the patient's parameters. In case of monitoring limits that are set too closely, this frequently leads to alarms regardless of whether a danger to the patient is present. However, a general weakening of the alarm limits is also not a suitable means for minimizing the alarm frequency here, since this would lead to a lower sensitivity of the monitoring. Provided that there is no contraindication and the remaining monitored parameters, for example, oxygen saturation or $CO_2$ partial pressure, during the monitoring of the breathing activity, lie within an acceptable range, a triggering of an alarm is dispensable in case of an at least only short-term over- or undershooting of the limit values. It follows from this that provided that no worsening of the state of the patient overall is recognized, an alarm-free toleration of a pathological breathing pattern rated as acceptable with regard to the patient's risk is permissible.

The minute volume represents an important parameter in the monitoring of the artificial ventilation of a patient. This value, which is used as a standard in medicine, for the air volume provided to the lung within one minute provides important evidence of the oxygenation and ventilation of a patient and is therefore an obligatory measured quantity for the monitoring of a patient in intensive care. In case of an exclusively mandatory ventilation of a patient, the minute volume corresponds to the product of the applied tidal volume and the respiratory rate.

However, no devices are currently known from the state of the art that analyze information about a concretely present breathing disorder. Hence, a distinction cannot be made between a supposed and an actual danger to the patient. Furthermore, the input possibilities for the alarm limits are limited and are oriented towards the technical monitoring of measured values instead of a patient-centered monitoring.

SUMMARY OF THE INVENTION

Based on the known state of the art as well as the problems described above, a basic object of the present invention is to provide a process as well as a device, which limits the number of sent alarms to the necessary minimum during an artificial ventilation of a patient, without increasing the danger potential of a patient. Thus, the present invention shall especially make it possible for limit values and delay times to be established, whereby properties of a special breathing pattern are taken into account and an interpretation with regard to the effects of hypopnea or apnea on the expected alarm frequency is given. Above all, in the case of special pathological breathing patterns, for example, Biot's breathing, it shall further be guaranteed that alarms, which occur only because of a special pathological form of breathing, but do not represent a danger to the patient, are suppressed. In this connection, a very special object lies in that the number of clinically irrelevant alarms is reduced during the monitoring of the expiratory minute volumes in patients with a special pathological form of breathing, especially with Biot's breathing.

The object described above is accomplished according to the present invention with a process as well as with a device. Further, a preferred implementation of the process according to the present invention is possible in respirators and anesthesia devices with a control device in accordance with the invention as well as with software implemented in a control device in accordance with the invention. Advantageous embodiments of the present invention are explained in detail in the following description with partial reference to the figures.

The present invention pertains at first to a process for generating an alarm during a machine-assisted ventilation of a patient, in which a minute volume is measured and a median of the minute volume is determined, and a lower critical limit value of the minute volume and a time delay, with which the sending of an alarm is generated after undershooting the lower critical limit value, are recorded in a control device.

According to the present invention, the process is further designed in such a way that, taking into account the lower critical limit value for the minute volume and the time delay based on the median of the minute volume, a reference signal is determined, from which are derived an alarm limit value (a limit value that when surpassed (undershot) results in/triggers an alarm) located below the lower critical limit value as well as a value for a maximum tolerated duration of apnea of the patient. The determined reference signal is a function of said lower critical limit value for the minute volume and said time delay and represents said limit value and said value for the maximum tolerated duration of apnea of the patient.

Furthermore, it is essential that an alarm signal is generated both during an undershooting of the lower critical limit value over a period of time that is longer than the established time delay and immediately during an undershooting of the alarm limit value.

The technical solution according to the present invention is thus at first characterized in that besides a lower alarm limit value for the minute volume, a critical interval is established, whereby depending on the status of the patient, a minute volume, whose value lies below the critical minute volume, but above the minute volume subject to alarm, is tolerated for a certain time.

With the range of the minute volume which is located between the lower critical value and the alarm limit value, a critical range of the minute volume is thus established, in which an alarm is not immediately sent, in which, however, a special monitoring provides us analysis of the further development of the minute volume. In this case, the minute volume is important evidence of the oxygenation and ventilation of a patient, which therefore represents a measured quantity obligatory for the monitoring of a patient in intensive care.

It should always be taken into account that in exclusively mandatory ventilation, the minute volume resulting from this is at least almost constant and is available at any time after one minute after the beginning of ventilation, while, in spontaneous breathing, an exact result can first be determined at the end of the time interval of one minute with the integration of the past period of time. Since both breathing efforts, which the patient has performed immediately before and those that lie one minute in the past, are reflected in the result, conclusions from the current breathing activity and possible danger, for example, hypopnea can only partly be drawn via such a calculated minute volume. In order to be able to use these parameters even in patients with pathological breathing patterns in a meaningful way despite these measured-value technical properties of the minute volume, a critical range is established according to the present invention, whereby an alarm signal is only sent if the value of the minute volume falls below the critical range or else the course of the minute volume has a special property, especially if it is not again located above the lower critical limit value even after an input tolerable time delay of the value of the minute volume.

Providing an additional critical range for the value of the minute volume is, above all, meaningful in the monitoring of an artificially ventilated patient, who has a special pathological form of breathing, for example, Biot's breathing, because in such a situation the case frequently arises in practice that the medical device generates an alarm signal, even though the patient is already breathing normally again. Such false alarms are reliably prevented when using the process according to the present invention.

Therefore, the process according to the present invention preferably ensures that during an irregular breathing, which is harmless for the patient, the monitored minute volume may briefly undershoot the set critical lower limit value, without an alarm signal being sent. An alarm signal would only be generated immediately after undershooting the alarm limit value or after the lower critical value of the minute volume was undershot longer than the present time delay.

When applying the process according to the present invention, first the minute volume of the patient is measured and a mean value of the minute volume formed via the median is determined from this. The median of the minute volume is advantageously determined by taking into consideration the spontaneous respiratory rate $f_{spon}$ as well as the spontaneous tidal volume $VT_{spon}$ over a preset time. The median is calculated in this case preferably via the sorting of all values to be averaged, whereby the result is that value which is in the middle in the sorted list. The use of the median value as special mean value is advantageous for this application, since it is robust against outlier values. Should the outlier values, especially partly due to apnea, be significant compared with spontaneous breathing, then, according to a preferred variant of the present invention, the corresponding values of the breathing intervals, which are substantially greater than the physiological pauses in breathing, are not taken into account.

In a special embodiment of the present invention, the maximum tolerated duration of apnea, which is determined on the basis of the reference signal, which arises from the calculated median of the minute volume, the input lower critical limit value of the minute volume as well as the also input tolerable time delay for sending an alarm after undershooting the lower critical limit value, is sent (output) optically and/or acoustically. Thus, the user is informed about which duration of apnea is tolerated based on the inputs carried out by the monitoring system before an alarm is sent (issued). In this way, it is possible for the user to check the duration of apnea determined and, for example, displayed on a monitor and tolerated by the monitoring system, taking into account the status of the patient and, if necessary, to change the value, set by it monitoring system, for the lower critical limit value of the minute volume and/or the set tolerable delay time.

According to the present invention, to determine the maximum tolerated duration of apnea as well as the alarm limit value of the minute volume, a reference signal is used, which represents a special step response, i.e., the time behavior of the output signal of a transmission member, and in particular of a filter used, in case of a signal change at the inlet. In this case, the step response represents a special signal at the outlet (output) of the filter, which follows a change in the minute volume or in the corresponding signal at the inlet (input) of the filter. A low-pass filter is preferably used as the filter. For generating the reference signal, values for the lower critical limit value set by the user as well as the tolerated delay time, i.e., the period of time within which no alarm is sent (issued) despite undershooting the lower critical limit value, and, on the other hand, for the measured minute volume are taken into account. Advantageously, the reference signal is generated in the analysis unit, by the output signal being received based on the median of the minute volume and based on the set values for the lower critical limit value as well as the maximum delay time. The reference signal in this case represents a special output signal of the filter, namely the signal, which follows an apnea of certain duration of a patient, who breathes or is ventilated with a median of corresponding value of the minute volume. Characteristic for the respectively determined reference signals, i.e., the step responses following an accepted apnea is that the functional curve first falls below the set lower critical limit value and then overshoots this limit value again after the set time delay. Based on the reference signal, which was determined by taking into account both the set values for a lower critical limit value as well as for a maximum delay time and of the median of the measured minute volume, the lower limit value of the minute volume subject to alarm resulting from this, on the one hand, and, on the other hand, the duration of apnea tolerated by the monitoring system in this case, within which no alarm is sent (issued), can be determined. Advantageously, the lower alarm limit value is determined in this case from the lower reversal point of the reference signal, which corresponds to the local minimum of the minute volume within the critical interval.

According to a special variant of the present invention, the reference signal is determined by means of hash tables, in which are recorded, on the one hand, values for the lower critical limit value of the minute volume as well as, on the other hand, for the time delay in case of the sending of an alarm after undershooting the lower critical minute volume value. According to a special embodiment of the present invention, values for the lower critical limit value of the minute volume are recorded in a first hash table and values for the time delay in the sending of an alarm after undershooting the lower critical minute volume value, the tolerated duration of apnea and for the alarm limit value are recorded in a second hash table. The tolerated duration of apnea, which would generate a corresponding reference signal, and the alarm limit value can be efficiently sought and determined with such a solution. The data may be recorded both in a data storage device of the analysis unit and in an external data storage device that is connected to the analysis unit via a data link.

Two hash tables are preferably provided for determining the ventilation-relevant parameters. In this case, a first hash table preferably contains a respectively unique index for the critical lower limit values of the minute volume which can be set by the user and a reference to the downstream second hash table. Parameters for the time delay in the sending of an alarm after undershooting the lower critical minute volume value, for the tolerable duration of apnea and for the lower limit value of the minute volume subject to alarm are recorded in the second hash table. In the carrying out of the corresponding settings, the user is basically free to input either a desired delay in the alarm sending or a tolerable duration of apnea in addition to the value for the critical minute volume. Based on the input parameters, a lower limit value of the minute volume subject to alarm as well as, depending on the input carried out, either a delay until the sending of an alarm or a tolerable duration of apnea is now determined by means of the second hash table.

The additional tolerance interval provided according to the present invention for the minute volume in turn lies between the lower critical limit value as an upper interval limit and the lower alarm limit value as a lower interval limit.

According to a special variant, the values for the lower critical limit value and/or for the alarm limit value are indicated in relation to the median of the minute volume. Advantageously, it is also conceivable that the user inputs or receives as output the lower critical limit value of the minute volume and the alarm limit value likewise as a percentage via a user interface, especially a monitor with a screen input option (so-called touchscreen).

In another special embodiment of the present invention, a course of the minute volume is analyzed with regard to special properties in a range between the lower critical limit value and the alarm limit value, i.e., within the interval for a critical range of the minute volume. If such an analysis is carried out, it is advantageously possible to carry out the generation of the alarm signal either even though the input time delay has not yet been reached, or else to delay even though the established time delay has already been reached based on such analysis.

According to a special variant of the above-described embodiment, the course of the minute volume is monitored within the critical range, i.e., between the lower critical limit value and the alarm limit value, by, above all, values for the first and/or second derivative of the functional curve of the minute volume being analyzed in this range. In this way, for example, an especially sharp drop of the minute volume may lead to an alarm even though the alarm limit value has not already been undershot and the time interval for the time delay for sending an alarm after undershooting the lower critical minute volume value has not already been overshot. In exactly the same way, the sending of an alarm signal is at first dispensed with in case of an only very low negative rise in the functional curve of the minute volume within this critical range and/or in case of an only very slight undershooting of the lower critical limit value although the tolerated time delay has already been overshot.

Furthermore, it is advantageous that information on a past course of the minute volume and/or on values of the minute volume, which are located below the lower critical limit value, but above the alarm limit value, are stored in reference to the present invention. In this connection, it is also conceivable that corresponding values are displayed or forwarded to an external device, for example, a monitor in a monitoring room. Furthermore, the alarms suppressed in the past, for example, because the minute volume was located within the critical range, but the critical range was left within the preset tolerated time delay, are graphically emphasized (highlighted) without an acoustical alarm signal having been generated before.

Furthermore, the present invention pertains to a control device that has elements for and is configured for implementing the process according to the present invention with at least one of the above-described process steps. The present invention also pertains to a control device/control system with software implementation therein for carrying out the process according to the present invention or one of the special embodiments based thereon.

Furthermore, the present invention also pertains to a device for monitoring a patient under machine-assisted ventilation with an input unit and with an output unit, with an analysis unit as well as with at least one data link for the data transfer between the analysis unit and a respirator. In this case, values of a measured minute volume can be fed to the analysis unit via the data link, whereby the analysis unit is designed (configured) such that a median of the minute volume can be determined on the basis of the measured minute volume. Furthermore, at least one lower critical limit value of the minute volume and a time delay, with which the sending of an alarm signal after undershooting the lower critical limit value is generated, can be input via a menu navigation of the input unit, and moreover, these values can be fed via the data link to the analysis unit. The analysis unit is designed (configured) such that alarm information is generated as soon as the minute volume undershoots the lower critical limit value. In this context, generation of an alarm information is defined as a corresponding information in relation to the limit value undershooting being generated in the monitoring system and recorded with data technology or being made available for a further data processing. By means of this action, the monitoring system is switched into a state of higher alertness, such that the further course of the minute volume up to an overshooting of the lower critical limit value is subject to a more intense monitoring, without an especially acoustical alarm signal being immediately sent. On the basis of the above-described alarm information, an alarm signal thus does not have to be sent immediately in any case as well.

The device designed according to the present invention is characterized in that at least one reference signal for the minute volume is recorded or determined in the analysis unit by taking into account the time behavior of a filter. Both an alarm limit value located below the lower critical limit value as well as a maximum tolerated duration of apnea of the patient can be determined on the basis of this reference signal based on the input values of the lower critical limit value of the minute volume and for the time delay, with which the sending of an alarm signal is generated after undershooting the lower critical limit value. An optically and/or acoustically perceptible alarm signal is sent via the output unit both during an undershooting of the lower critical limit value for a period of time which is longer than the established time delay and during an undershooting of the alarm limit value.

Values for the lower critical limit value, the alarm limit value, the time delay, with which the sending of an alarm is generated after undershooting the lower critical limit value, as well as the duration of apnea in hash tables tolerated by the user, in each case taking into account the status of the patient, are preferably recorded in the analysis unit and/or in a data storage device connected to same. Furthermore, it is conceivable that historical information about a past course of the minute volume and/or about values of the minute volume which were found below the lower critical limit value but above the alarm limit value, i.e., within the critical interval which is preferably under special observation, can be filed away in the analysis unit and/or in a data storage device connected to same. Such information about the course and special events of the minute volume can preferably in turn be displayed via an output unit or can be forwarded to a data processing unit.

Without limiting the general idea of the present invention, the present invention is explained in detail below on the basis of exemplary embodiments with reference to the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 6a is a view of a minute volume course for a comparison of the minute volume with the related reference signal;

FIG. 6b is a view of another minute volume course for a comparison of the minute volume with the related reference signal;

FIG. 6c is a view of the reference signal;

DESCRIPTION OF THE PREFERRED EMBODIMENTS

Figure 1A:
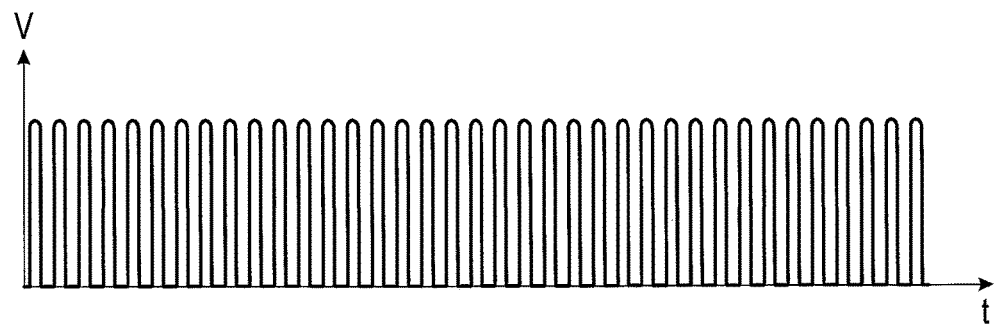
FIG. 1a is a graphic representation of a normal breathing.
Figure 1B:
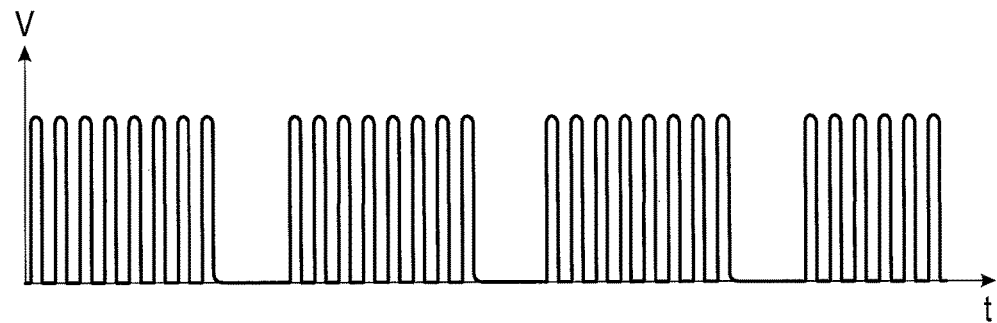
FIG. 1b is a graphic representation of one of various forms of pathological breathing.
Figure 1C:
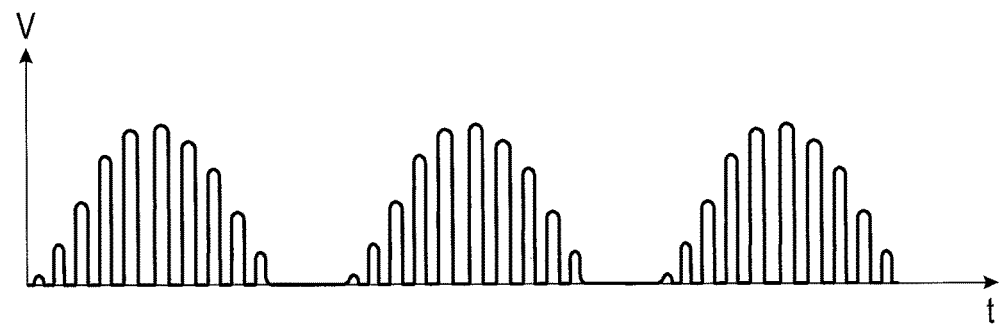
FIG. 1c is a graphic representation of another of various forms of pathological breathing.
Figure 1D:
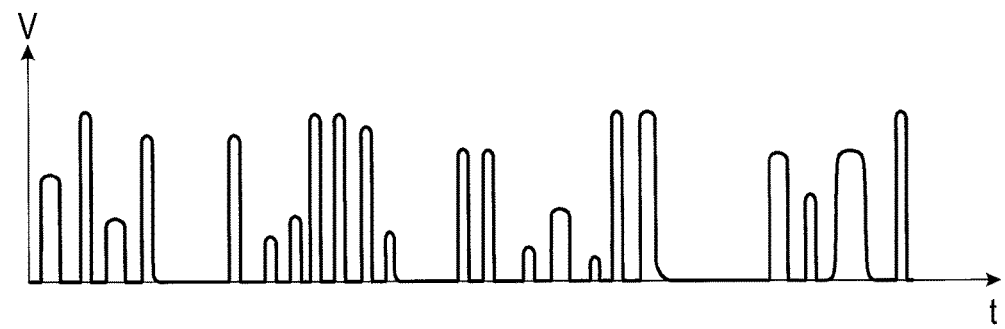
FIG. 1d is a graphic representation of another of various forms of pathological breathing.

Referring to the drawings, the course over time of normal breathing (FIG. 1a) is graphically compared to the courses of three different pathological forms of breathing (FIGS. 1b, 1c, 1d). While FIG. 1a shows the course over time of normal breathing in relation to the inhaled and exhaled volume, FIGS. 1b-1d contain representations of Biot's breathing, Cheyne-Stokes breathing as well as ataxic breathing.

Cheyne-Stokes breathing (FIG. 1c) is characterized in that the individual breaths follow a wave shape. This means that the tidal volumes are at first greater and weaker and episodes of apnea lie between these individual breaths. The respiratory rate may also vary in this case.

In comparison to this, the breaths of ataxic breathing shown in FIG. 1d differ in their volume and frequency, whereby here as well the breathing activity can be interrupted by longer pauses, i.e., episodes of apnea.

It is essential to the Biot's breathing shown in FIG. 1b that a sequence of uniform and sufficiently deep breaths is interrupted by sudden episodes of apnea. Biot's breathing occasionally occurs in premature babies and newborns because of immaturity of the breathing center. In this case, damage to the breathing center, elevated brain pressure, meningitis, meningo-encephalitis or craniocerebral trauma are considered to be pathological causes. The technical solution according to the present invention, which will be explained in detail below, is suitable, above all, in the monitoring of the pathological forms of breathing described above and here more particularly for the monitoring of the ventilation of a patient with Biot's breathing.

In case of the monitoring of the ventilation of a patient, the so-called minute volume MV is usually monitored. Here, different limit values, which lead to an alarm by the monitoring system, can be set for the user. It is important for an effective monitoring of a ventilated patient that the number of alarms sent that are clinically irrelevant be minimized.

An alarm is classified as clinically irrelevant if, on the one hand, the status of the patient is known and no worsening has developed since the establishment of this status. Thus, the monitored minute volume could overshoot or undershoot a set limit value during an irregular breathing, without this leading to a danger to the patient. An alarm is undesired in such a case. If, on the other hand, the limit value is infringed for a longer time, then an alarm is absolutely necessary.

If a patient has a pathological form of breathing with apnea between the individual breathing cycles, the clinically irrelevant alarms mentioned above often occur. This can be attributed to the fact that episodes of apnea appear to be delayed in the calculated value because of the filtering of the minute volume. Consequently, situations, in which the breathing of the patient does not correspond with the currently calculated minute volume, may occur, such that an alarming of the minute volume asynchronous to the breathing activity of the patient occurs in case of an irregular breathing. An alarm thus occurs when the patient is breathing again; however, a currently pending apnea does not trigger an alarm because of the monitoring of the minute volume.

Figure 2:
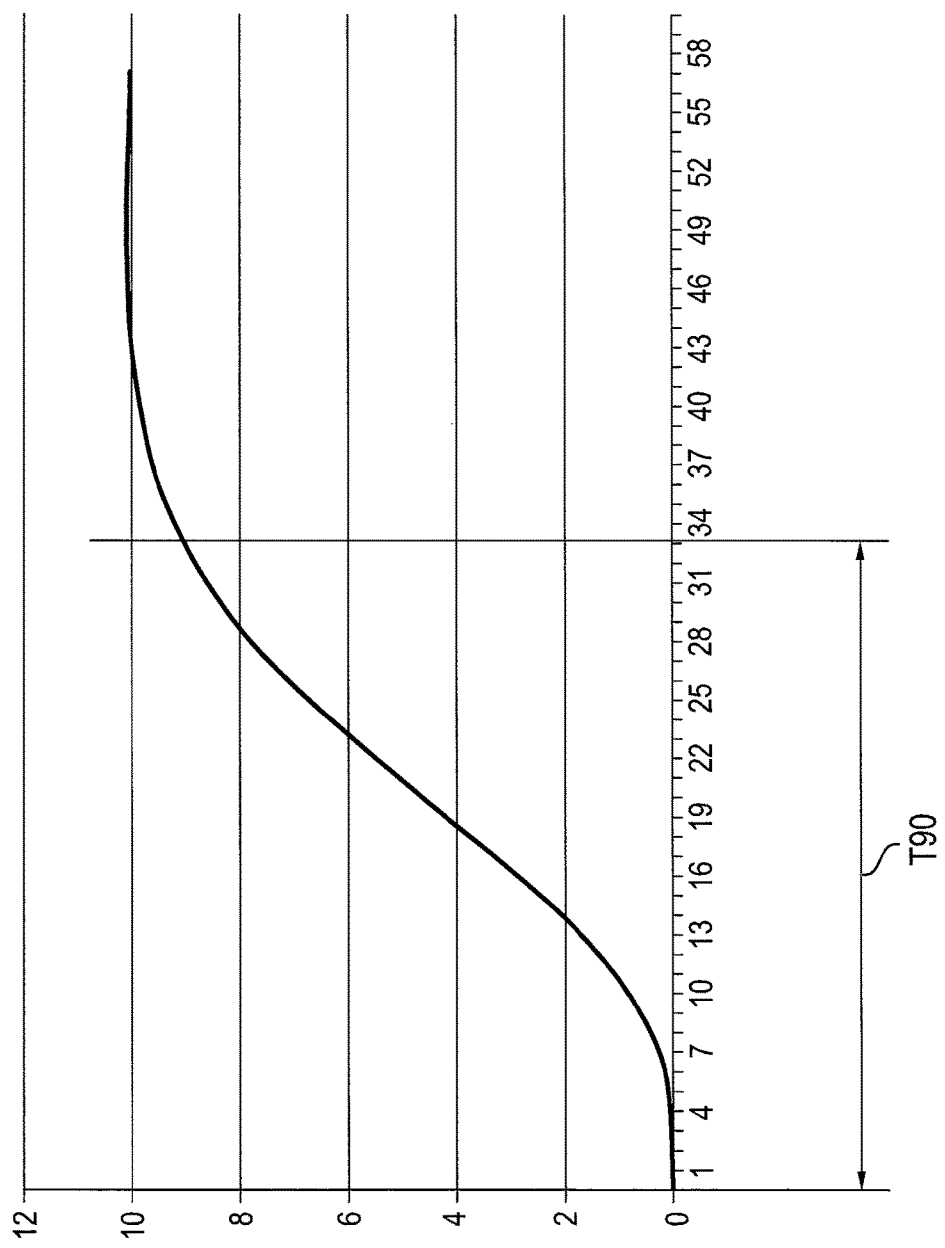
FIG. 2 is a graphic representation of the step response of a low-pass filter order with T90=33 sec.

FIG. 2 shows the step response of a low-pass filter with a time value T90. The step response of this filter, which is preferably used in the monitoring of the minute volume of a ventilated patient, represents the time behavior of the filter output signal in case of a signal change at the inlet, in this situation in case of a change in the minute volume. The filter used is clearly characterized in its properties by the step response shown in FIG. 2. In this case, the T90 time is an indicator of the delay, with which the input signal has an effect on the output signal. The reference signal, which is explained in detail below, which is used as the basis ultimately in the determination of a lower alarm limit value as well as of a duration of apnea tolerated by the monitoring system until the sending of an alarm, represents the output signal at the filter depending on a change in the input signal, namely the minute volume. Even though the discussion below always starts with the use of a low-pass filter, the process according to the present invention can basically be used regardless of the type of filter used, the order and the T90 time.

Figure 3:
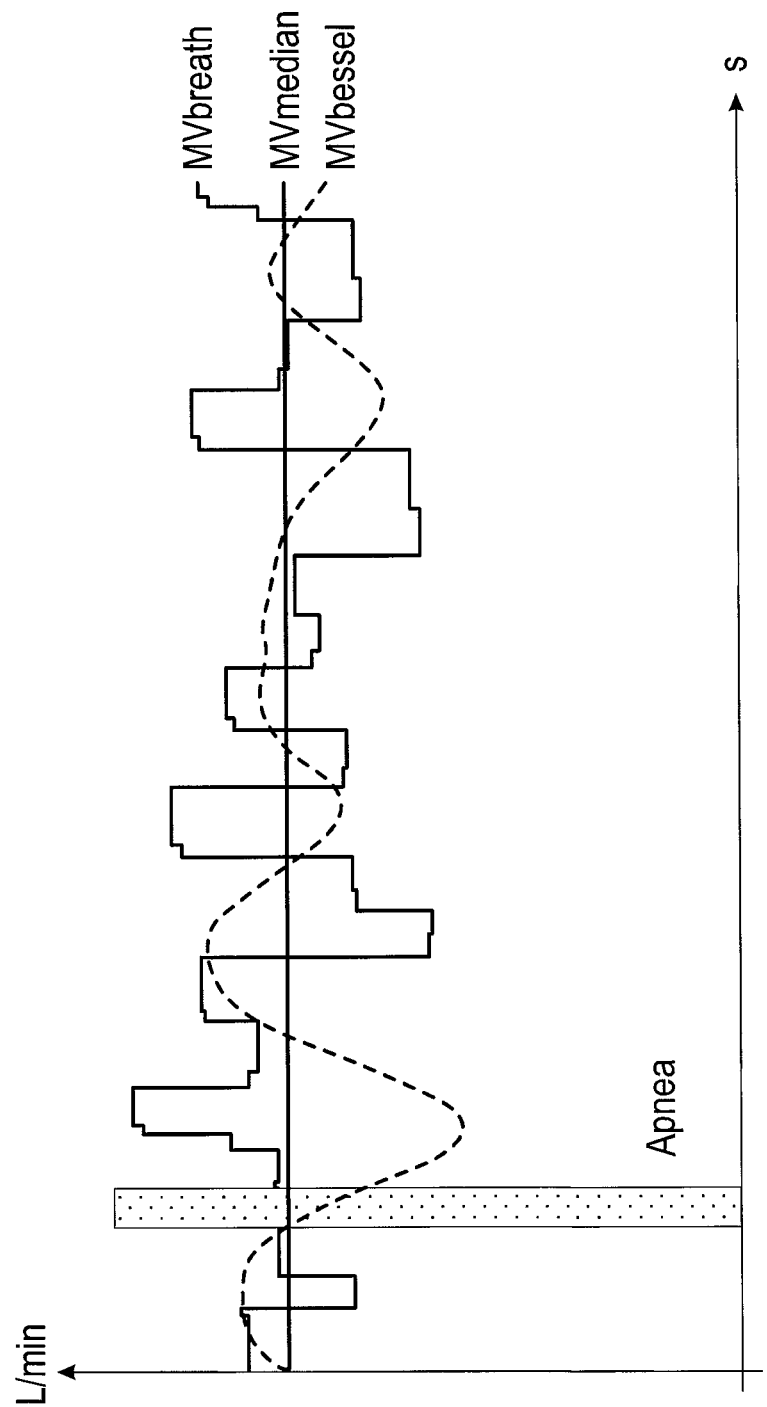
FIG. 3 is the course of the minute volume of an artificially ventilated patient (baseline calculation)

FIG. 3 shows the course over time of the minute volume of a breathing, the output signal brought about by this at the filter of the measuring unit, as well as the median of the minute volume. The calculation of the median of the minute volume is not based on the integration and filtering of the actual air stream, but rather on a multiplication of mean rate $f_{spon}$ and mean tidal volume $VT_{spon}$ during a normal breathing.

$$MVmedian = \overline{fspon} \cdot \overline{VTspon},$$

in which $\overline{VTspon}$ is the median of the measured tidal volumes over a preset time $t$ and $\overline{fspon} = \dfrac{1}{\overline{Tcycle}}$.

Here, $\overline{Tcycle}$ corresponds to the median over all determined breathing cycle times over the same period of time t.

The calculation of the median occurs via the sorting of all values to be averaged, whereby the result is that value which is in the middle in the sorted list. Compared to other mean value calculations, the median has the decisive advantage that it is robust against outliers. Should the outliers, in this case the episodes of apnea occurring in the patient, be significant compared to spontaneous breathing, then the corresponding period durations, which are substantially greater than the physiological pauses in breathing, may not be taken into account.

Figure 4:
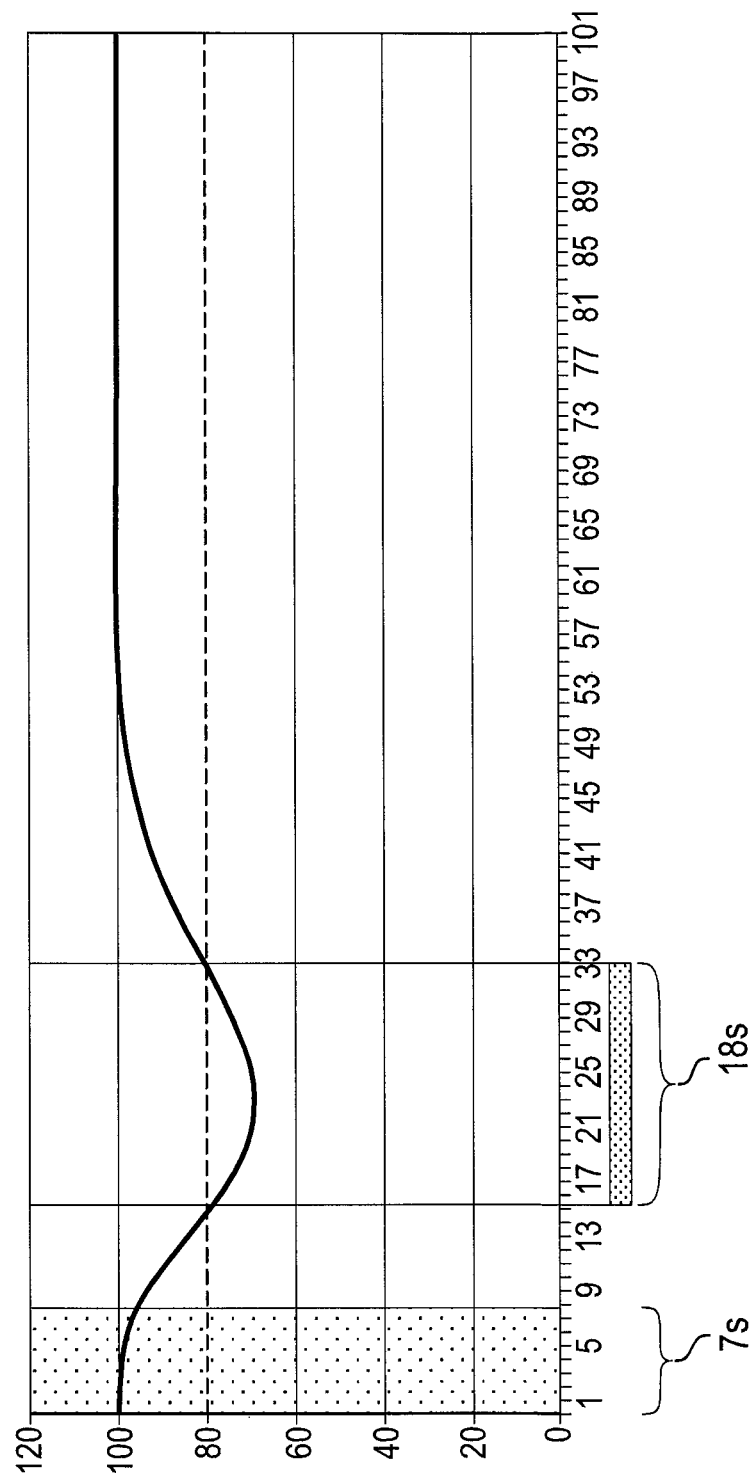
FIG. 4 is a view of the course of the calculated minute volume with a tolerated apnea of 7 sec. (alarm duration: 18 sec.)

FIG. 4 shows the course over time of the minute volume after the occurrence of apnea. As can be clearly recognized, the course of the minute volume with marked time delay reacts to the apnea that has occurred previously. In the example shown, the apnea has a duration of 7 sec. Only after about 5 sec., the value of the minute volume drops slightly and finally drops about 24 sec. after the beginning or 17 sec. after the end of the apnea to a minimum value, which is about 70% of the original minute volume. Depending on a limit value which is usually established for the minute volume, an alarm would clearly take place after the apnea is past in the prior-art systems. For this reason, the monitoring process according to the present invention provides, besides a lower alarm limit value, in case of whose undershooting an alarm signal is absolutely generated, a further lower critical limit value of the minute volume, which is set by the user depending on the status of the patient above the alarm limit value. The user sets this lower critical limit value for the minute volume, in case of whose undershooting an alarm signal is not yet immediately generated depending on the status of the patient. Furthermore, the user sets a value for a time delay, after which an alarm signal is sent after undershooting the lower critical limit value, or the tolerable duration of apnea. If, in this case, the minute volume falls below the lower critical limit value, but it overshoots it again within the input period of time for the time delay, then no alarm signal is sent by the monitoring device. This corresponding status is only documented in a data storage device.

Based on the input values for the lower critical limit value of the minute volume as well as based on a tolerated time delay in the triggering of an alarm, a filter-dependent reference signal is generated in the monitoring system, taking into account (that is a function of) the minute volume. Based on this reference signal, the system now determines, on the one hand, a tolerated duration of apnea, in case of whose appearance a corresponding signal would be generated, and, on the other hand, the lower limit value of the minute volume subject to alarm, which arises from the local minimum of the reference signal.

The reference signal is determined by the analysis unit of the monitoring system based on a value for the median of the minute volume. The use of a median of the minute volume as a starting point for the reference signal is suggested, since the starting point used for the calculation of the reference signal should correspond to the average minute volume during a spontaneous normal breathing. A normal breathing in this connection is defined as a breathing, which does not have further episodes of apnea between inhalation and exhalation aside from the pauses in breathing.

Figure 5:
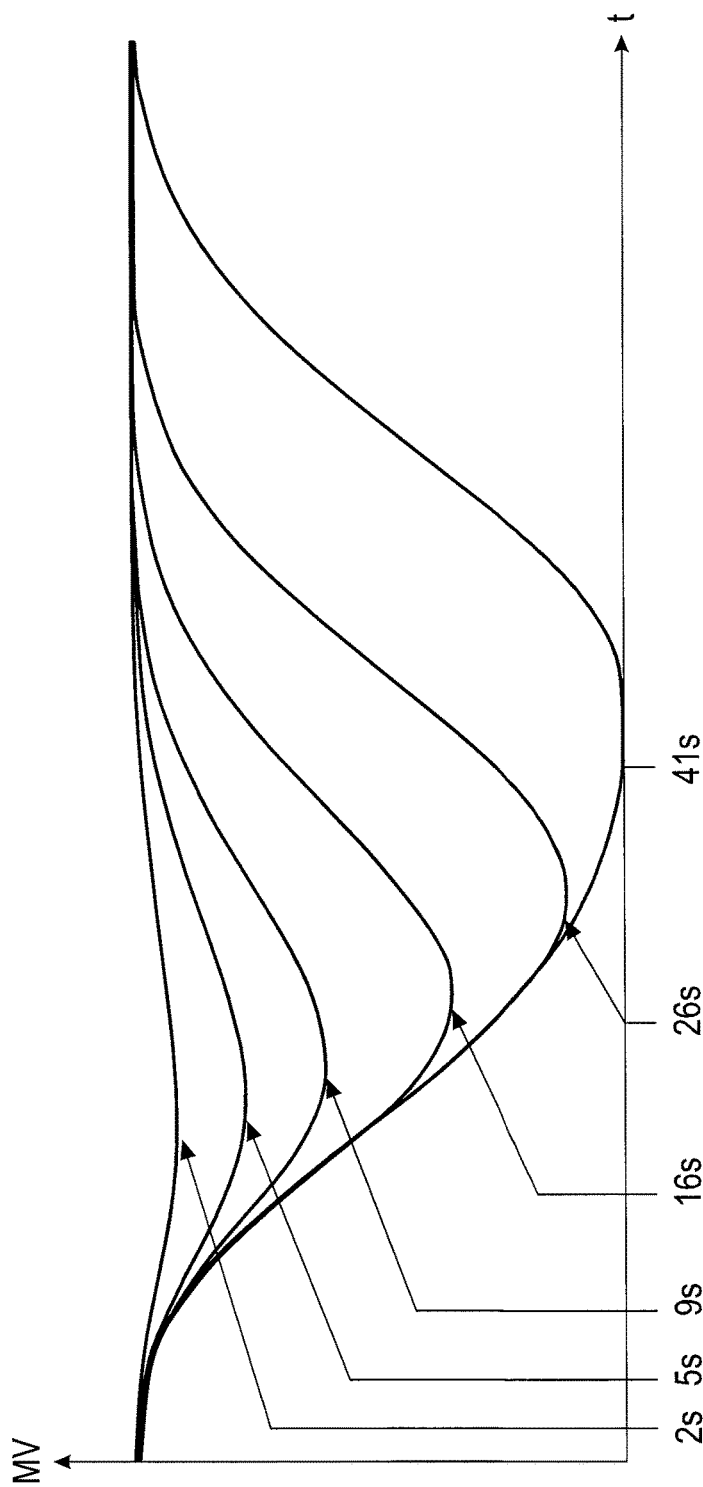
FIG. 5 is exemplary manifestations of the apnea times 2 sec., 5 sec., 9 sec., 16 sec., 26 sec. as well as 41 sec. on the determined minute volume MV.

The determination of the critical range, i.e., of the interval between the lower critical limit value and the alarm limit value, is shown, for example, in FIG. 5. In this connection, FIG. 5 shows different reference signals, which would be formed based on a value for the minute volume for tolerated episodes of apnea with a duration of 2, 5, 9, 16, 26 and 41 sec., respectively. Since the reference signal ultimately represents the response, generated via the filter of the measuring device, to the minute volume used as the input signal, the analysis unit of the measuring device will also generate identical reference signals in case of episodes of apnea of identical length. The reference signal used according to the present invention thus represents a system response, which is used for a comparison with the course over time of the minute volume.

The basic idea of the present invention, namely determination of an additional lower critical limit value for the minute volume, which does not immediately lead to the sending of an alarm signal, is that the user can at first preset a value for the lower critical value as well as a tolerable time delay for sending an alarm after undershooting the lower critical limit value depending on the status of the patient. Based on the median of the minute volume, the analysis unit then generates a reference signal and determines the alarm limit value and a duration of apnea tolerated by the monitoring system based on the settings made.

The resulting distance between the lower critical limit value and the alarm limit value lying below it, which corresponds to the minute volume in the lower reversal point of the reference signal, is the critical range of the minute volume. Provided that the minute volume of a ventilated patient lies only briefly in this critical range, the minute volume thus drops to a value between the lower critical limit value and the alarm limit value, but again overshoots the lower critical limit value within the preset delay for an alarm, an alarm is not sent. If the minute volume drops below the lower critical limit value over a longer period of time, e.g., because of a hypopnea, however, an alarm signal is also sent if the value for the minute volume does not drop below the alarm limit value.

In FIGS. 6a, 6b and 6c, two different minute volume courses (FIGS. 6a and 6b) are compared to a reference signal (FIG. 6c) in this connection. The reference signal according to FIG. 6c results from the setting of a lower critical limit value of 7.5 L/min as well as a delay time of 35 sec. An alarm limit value of 1.8 L/min as well as a duration of apnea of 21 sec. tolerated by the monitoring system without alarm follow these pre-settings. The input delay time, which corresponds to a maximum tolerated residence time of the minute volume within the critical range, is shown as an arrow in FIGS. 6a through 6c, respectively. Via the respective settings of the lower critical limit value as well as the delay time until the sending of an alarm, the user, taking into account the status of the patient, is able to determine which breathing interruptions (episodes of apnea) are tolerated and which ones lead to an alarm.

While an alarm is not triggered in case of the course of the minute volume following an episode of apnea shown in FIG. 6a, an alarm is triggered in case of the course according to FIG. 6b, even though the value for the minute volume has not fallen below the alarm limit value. In FIG. 6a, the minute volume drops below the lower critical limit value, but overshoots it again before the input delay time of 35 sec. for the sending of an alarm when undershooting of the lower critical limit value is reached. On the other hand, in the case shown in FIG. 6b, the minute volume drops to the same value as in FIG. 6a, but the value of the minute volume rises more slowly, such that finally the set delay time is overshot and the sending of an alarm is triggered.

Figure 7A:
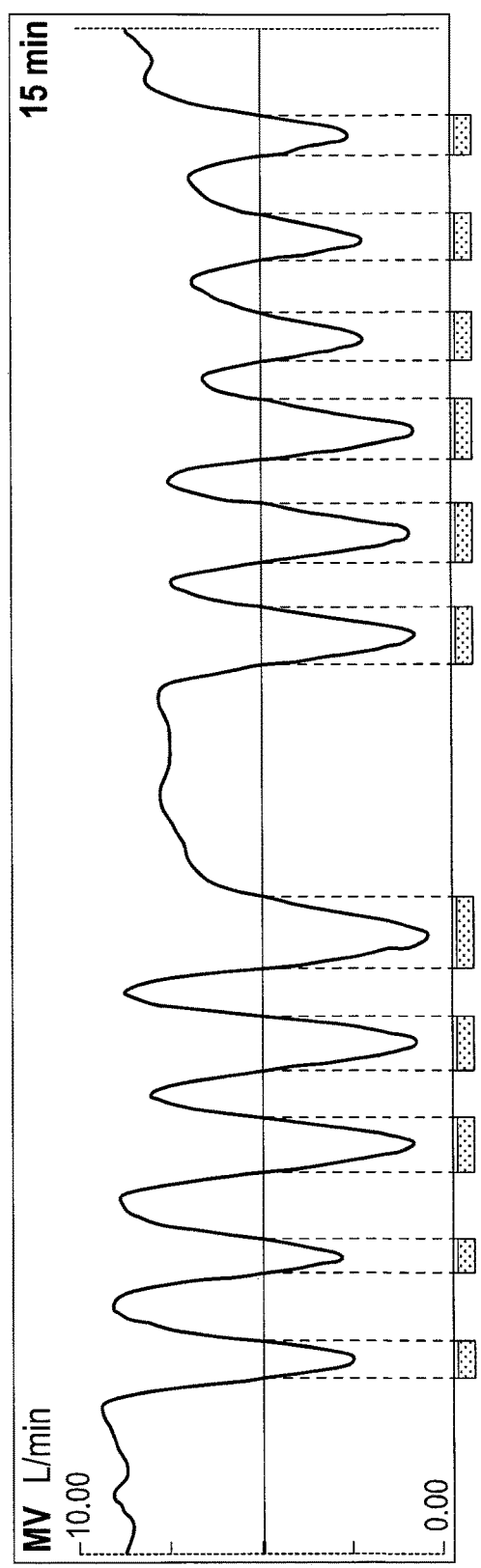
FIG. 7a is a view showing a limit value setting.
Figure 7B:
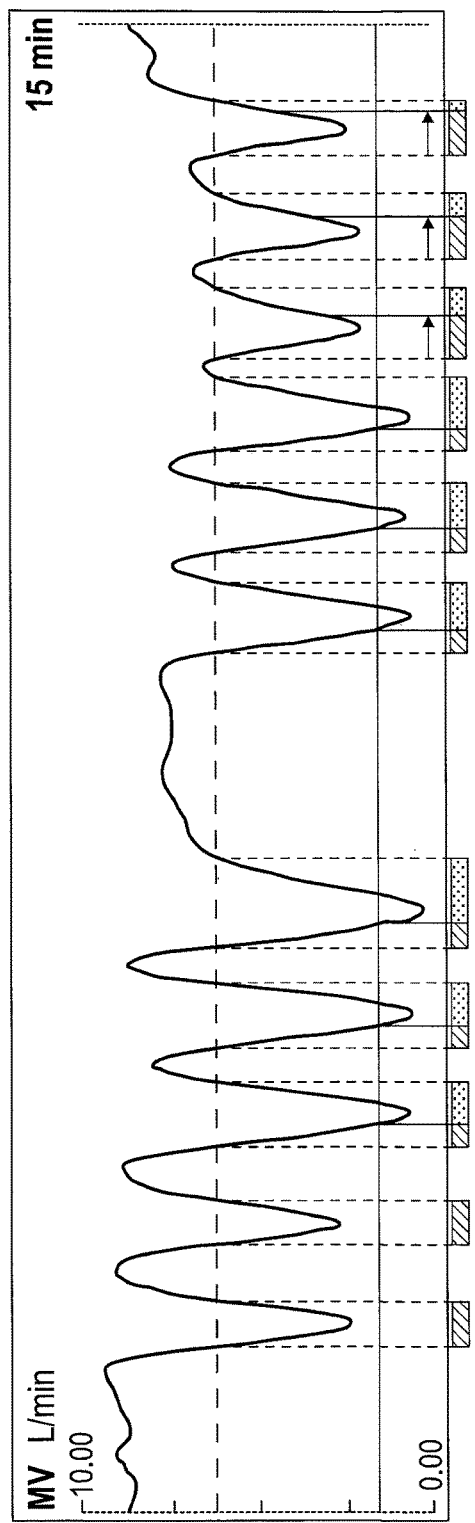
FIG. 7b is view showing an exemplary setting of a critical range.

Furthermore, FIGS. 7a and 7b show the course of the value of the minute volume sent at the outlet of the filter of the measuring unit in a graphic view. Here, each of the horizontal solid lines represent an alarm limit value, whereby it is a limit value setting according to FIG. 7a, as it is known from the state of the art, while according to FIG. 7b, in addition to the alarm limit value, a critical range for the minute volume is set.

In the case of the setting shown in FIG. 7a, each undershooting of the alarm limit value results in a sending of an acoustical signal, which, on the one hand, leads to a considerable stress to the patient, and, on the other hand, increases the risk that the hospital staff does not detect relevant alarms because of the plurality of alarms. At the same time the alarm times are comparatively long.

In case of a setting of the limit values according to FIG. 7b, a lower critical limit value is provided in addition to the alarm limit value. Between these limit values lies a critical range of the minute volume. If the minute volume drops to a value in this range, an alarm is triggered only if the value drops further below the alarm limit value or if the value does not overshoot the lower critical limit value again within the set delay time. The number of acoustical alarms is markedly reduced, without it representing a risk for a patient with a pathological form of breathing, and the respective alarm duration is shortened.

Figure 8:
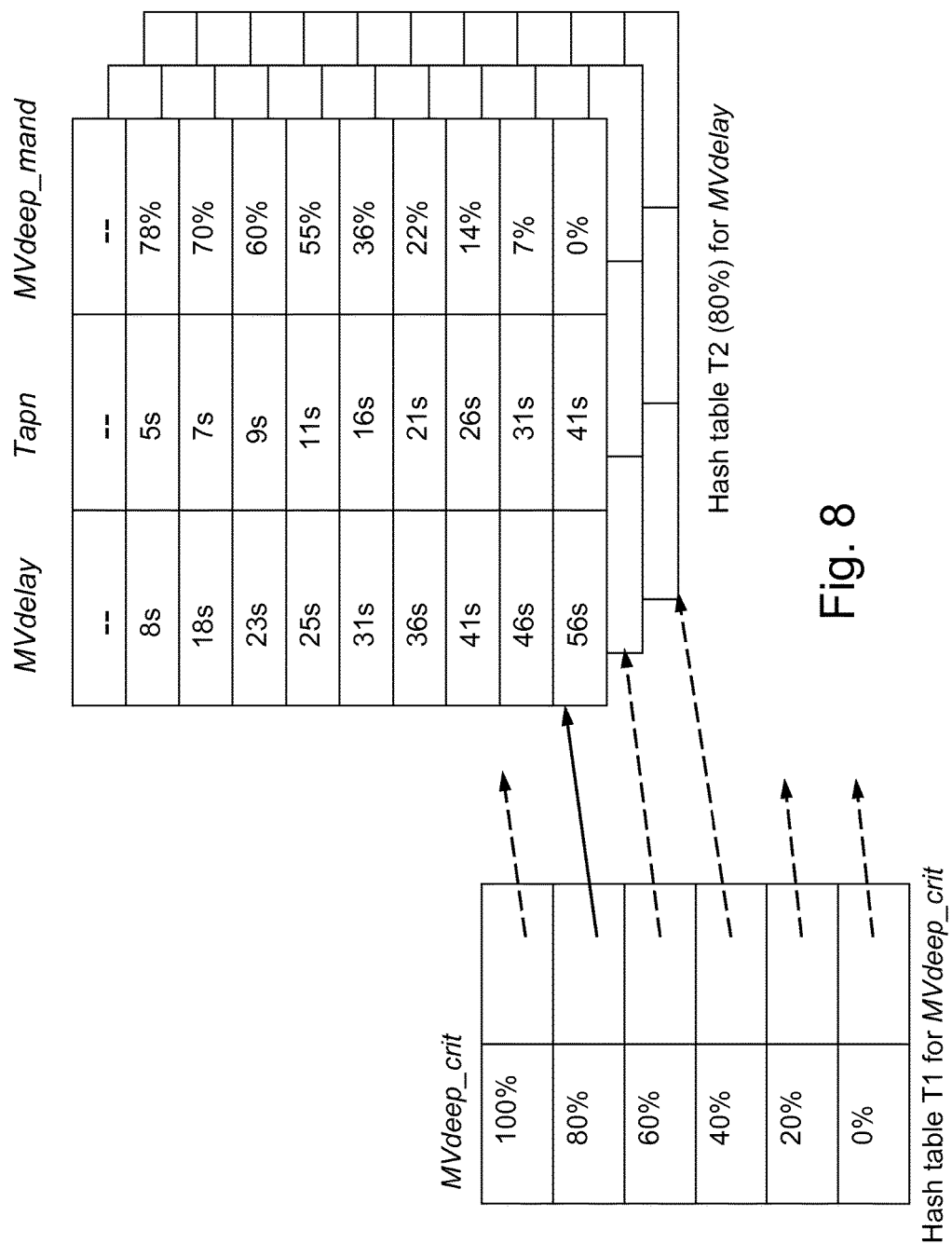
FIG. 8 is a view of hash tables for the efficient determination of the resulting duration of apnea as well as the MVmandatory values from the given MVcrit and Mvdelay.

Various hash tables, as they are shown in FIG. 8, are used for the determination of the reference signal. Among other things, the values for the duration of apnea and the alarm limit value are recorded in these tables. The hash table T1 contains for the settable value of the lower critical limit value of the minute volume a respective unique index and a reference to the downstream hash table T2 with the parameters for the settable delay time and the values for the tolerated duration of apnea and the lower alarm limit value belonging thereto. As is shown in FIG. 8, T1 contains the value for the settable lower critical limit value of the minute volume in the left column, whereby this is indicated proportionately in percent of the median of the minute volume. In the left column, T2 contains the settable delay time for alarm suppression and ascending sorted values for the duration of apnea or the limit value of the minute volume subject to alarm in columns 2 and 3, respectively. If the value 80% is selected by the user for the lower critical limit value, then the corresponding value in the hash table T2 is accessed via the hash table T1. Provided that the user has, moreover, selected a permissible delay time for an alarm suppression of, for example, 23 sec., a time duration of 9 sec. results for the tolerated duration of apnea, and a minute volume, which corresponds to 60% of the median value, results for the alarm limit value.

The delay time input by the user is used in the hash table T2 as the search key within the table. The sought values for the tolerated duration of apnea and the alarm limit value are found in the same line of the table. For minimizing the memory requirements for the hash tables, not all the settable values for the lower critical minute volume value and the delay time are recorded, but rather only a sufficient number of grid points for accuracy, via which the sought values can be determined by means of interpolation. Thus, it is possible to determine, for example, the missing entries for the hash table T1 by the tolerated duration of apnea and the alarm limit value both for the next higher and the next lower critical limit value parameters contained in Table 1 being determined and then interpolated.

Figure 9:
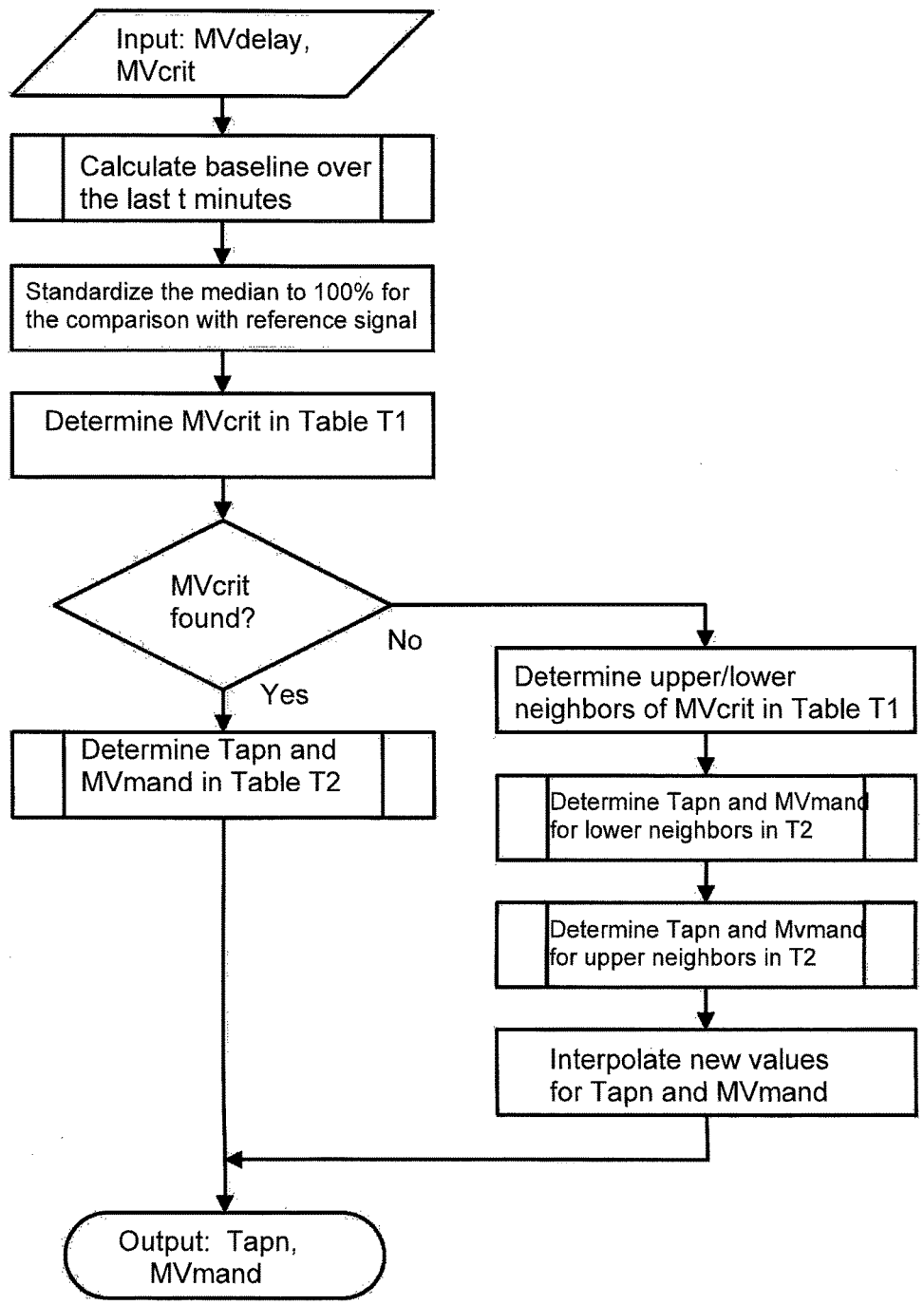
FIG. 9 is a flow chart for determining the lower limit value for the minute volume subject to alarm as well as the tolerable duration of apnea.

FIG. 9 shows a flow chart for carrying out the process according to the present invention. At first, the user has the possibility to input values for the lower critical limit value and the delay time via an input unit into the monitoring system. The median of the minute volume is calculated on the basis of the determined minute volume of the ventilated patient and standardized to a value of 100% for the comparison with the reference signal. Based on the determined median and the values input by the user, the analysis unit generates a reference signal.

Provided that a value for the lower critical limit value is found in the hash table T1 recorded in the analysis unit, the corresponding values for the alarm limit value and the duration of apnea tolerated by the monitoring system at the selected settings are directly determined by means of hash table T2. These are sent to the user, so that it can be checked whether the corresponding values and settings are reasonable for the patient to be ventilated.

If a value for the lower critical limit value cannot be directly found in the hash table T1, a tolerated duration of apnea and the alarm limit value are determined and then interpolated both for the next higher and the next lower critical limit value parameters contained in Table T1. The values for the alarm limit value obtained based on the interpolation and the duration of apnea tolerated by the monitoring system at the selected settings are in turn sent to the user.

Figure 10:
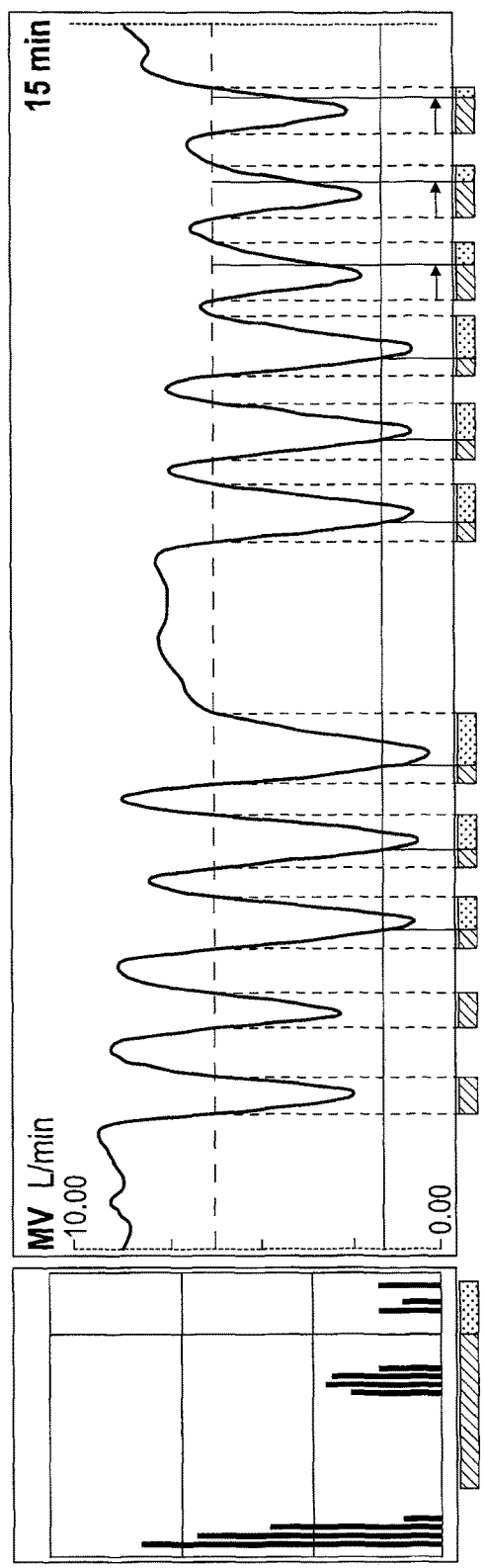
FIG. 10 is the determination and graphic representation of the pauses in breathing.

FIG. 10 shows the representation of pauses in breathing or episodes of apnea on a display, whereby the representation form shown according to this exemplary embodiment is combined with the process according to the present invention to delay the sending of an alarm. The course of the minute volume is plotted over a period of time of 15 minutes in the diagram on the right side. The lower critical limit value is in turn characterized with a horizontal, dashed line, while the limit subject to alarm is shown by means of a solid line. The course of the curve of the minute volume results from a breathing of a patient with a pathological breathing pattern. In this case, the patient is breathing with the so-called Biot's breathing, which is characterized by a plurality of regular breaths followed by a long pause in breathing.

In order to minimize the number of alarms that are brought about because of the pauses in breathing typical for Biot's breathing, a critical range for the minute volume that is located between the lower critical limit value and the alarm limit value is in turn recorded in the control device. An acoustical alarm is only sent if the value for the minute volume drops below the alarm limit value or does not overshoot the lower critical limit value again within the delay time. If an alarm is triggered because of an undershooting of the alarm limit value, this alarm is canceled again when the value of the minute volume overshoots the lower critical limit value. Corresponding alarm times are shown as horizontal bars under the right diagram. Here, striped bars represent a period of time, in which the minute volume has been within the critical range. On the other hand, periods of time, in which an acoustical alarm was sent, are shown by completely filled bars.

In addition to the course of the minute volume, the representation according to FIG. 10 contains a histogram on the left side, which shows the frequency of the occurrence of pauses in breathing or episodes of apnea. In this histogram the x axis describes the duration of the pauses in breathing and episodes of apnea. On the other hand, the y axis contains the information about the frequency of the occurrence of corresponding pauses in breathing or episodes of apnea, whereby the representation is usually logarithmic. The range of the x axis can be split into three ranges, namely a left range, in which natural pauses in breathing, i.e., with a duration of a few seconds, are shown, a middle range, in which tolerable episodes of apnea that lead to a minute volume lying within the critical range are detected, and a right range, in which episodes of apnea that appeared during the observation period which lead to a minute volume that lies below the range subject to alarm are plotted. Thus, the representation shown in FIG. 10 contains a comparison of the course of a minute volume over an observation period, here 15 minutes, as well as a histogram, in which the frequencies of the pauses in breathing and episodes of apnea that occurred in this period, and are split into natural, tolerable and intolerable pauses in breathing, are detected and visualized. Because of this representation, it is possible for the user in a comparatively simple way to recognize the breathing pattern and the status of the ventilated patient and to take corresponding actions if necessary. The sending of acoustical alarms is also in turn limited to a minimum classified as sufficient by the user.

While specific embodiments of the invention have been shown and described in detail to illustrate the application of the principles of the invention, it will be understood that the invention may be embodied otherwise without departing from such principles.

What is claimed is:

1. A process for generating an alarm during a machine-assisted ventilation of a patient, the process comprising the steps of:

measuring a minute volume during machine-assisted ventilation of a patient;

determining a median of the measured minute volume;

inputting a lower critical limit value of the minute volume and inputting a time delay, with which time delay an alarm is generated after undershooting the lower critical limit value of the minute volume, in a control device;

determining with the control device a reference signal that is a function of the input lower critical limit value for the minute volume and the input time delay based on the determined median of the minute volume, from which reference signal are derived an alarm limit value located below the lower critical limit value as well as a maximum tolerated duration of apnea of the patient; and generating an alarm signal during the machine-assisted ventilation of the patient both during an undershooting of the lower critical limit value for a period of time that is longer than the input time delay and during an undershooting of the alarm limit value.

2. A process in accordance with claim 1, wherein the determined maximum tolerated duration of apnea is issued optically and/or acoustically.

3. A process in accordance with claim 1, wherein the reference signal is determined on the basis of a time behavior of a filter being used in the measurement of the minute volume.

4. A process in accordance with claim 1, wherein the reference signal is determined on the basis of ventilation and/or breathing parameters of the patient measured during the ventilation.

5. A process in accordance with claim 1, wherein the reference signal is determined by means of hash tables, in which values for the lower critical limit value of the minute volume as well as for the maximum tolerable duration of apnea are input.

6. A process in accordance with claim 1, wherein pauses in breathing of the patient are determined and information about the pauses in breathing are stored in a data storage device and/or graphically displayed on an output unit.

7. A process in accordance with claim 1, wherein values for the lower critical limit value and/or values for the alarm limit value are indicated and/or input in relation to the median of the minute volume.

8. A process in accordance with claim 1, wherein a course of the minute volume is analyzed in a range between the lower critical limit value and the alarm limit value, and taking the analysis into account, the alarm signal is generated, even though the established time delay is not yet reached, or is delayed even though the established time delay has already been reached.

9. A process in accordance with claim 1, wherein information on a past course of the minute volume and/or on values of the minute volume, found to be below the lower critical limit value but above the alarm limit value, is stored.

10. A process in accordance with claim 1, wherein the information on a past course of the minute volume and/or on values of the minute volume, which were found below the lower critical limit value but above the alarm limit value, is displayed and/or transmitted to an external device.

11. A process for generating an alarm during a machine-assisted ventilation of a patient, the process comprising the steps of:
measuring a minute volume during machine-assisted ventilation of a patient;
determining a median of the minute volume;
inputting a lower critical limit value of the minute volume and inputting a maximum tolerated duration of apnea of the patient in a control device;
determining with the control device a reference signal that is a function of the input lower critical limit value for the minute volume and the input maximum tolerated duration of apnea based on the median of the minute volume, from which are derived an alarm limit value located below the lower critical limit value as well as a time delay, with which time delay an alarm is issued after undershooting the lower critical limit value; and
generating an alarm signal during the machine-assisted ventilation of the patient both during an undershooting of the lower critical time value for a period of time that is longer than the established tolerated duration of apnea and during an undershooting of the alarm limit value.

12. A process in accordance with claim 11, wherein the determined time delay, with which an alarm is issued after undershooting the lower critical time value, is sent optically and/or acoustically.

13. A process in accordance with claim 12, wherein values for the lower critical limit value of the minute volume are recorded in a first hash table and values for the time delay, the maximum tolerated duration of apnea and for the alarm limit value are recorded in a second hash table.

14. A process in accordance with claim 11, wherein the reference signal is determined on the basis of a time behavior of a filter being used in the measurement of the minute volume.

15. A process in accordance with claim 11, wherein the reference signal is determined on the basis of ventilation and/or breathing parameters of the patient measured during the ventilation.

16. A process in accordance with claim 11, wherein the reference signal is determined by means of hash tables, in which values for the lower critical limit value of the minute volume as well as for the maximum tolerable duration of apnea are input.

17. A process in accordance with claim 11, wherein pauses in breathing of the patient are determined and information about the pauses in breathing are stored in a data storage device and/or graphically displayed on an output unit.

18. A process in accordance with claim 11, wherein values for the lower critical limit value and/or values for the alarm limit value are indicated and/or input in relation to the median of the minute volume.

19. A process in accordance with claim 11, wherein a course of the minute volume is analyzed in a range between the lower critical limit value and the alarm limit value, and taking the analysis into account, the alarm signal is generated, even though the established time delay is not yet reached, or is delayed even though the established time delay has already been reached.

20. A process in accordance with claim 11, wherein information on a past course of the minute volume and/or on values of the minute volume, found to be below the lower critical limit value but above the alarm limit value, is stored.

21. A process in accordance with claim 11, wherein the information on a past course of the minute volume and/or on values of the minute volume, which were found below the lower critical limit value but above the alarm limit value, is displayed and/or transmitted to an external device.

22. A control device, for generating an alarm during a machine-assisted ventilation of a patient, the control device being configured to execute a process comprising the steps of:
receiving measured minute volume values during the machine-assisted ventilation of the patient;
determining a median of the measured minute volume;
receiving a lower critical limit value of the minute volume input setting and the receiving another input setting that is one of a time delay input setting, with which time delay an alarm is generated after undershooting the lower critical limit value and a maximum tolerated duration of apnea input setting in the control device;
determining a reference signal that is a function of the lower critical limit value for the minute volume input setting and said another input setting that is one of:
the time delay, based on the median of the minute volume; and
the maximum tolerated duration of apnea based on the median of the minute volume, from which are derived an alarm limit value located below the lower critical limit value as well as the time delay, with which an alarm is issued after undershooting the lower critical limit value; and generating an alarm signal during an undershooting of the alarm limit value by the measured minute volume and also during an undershooting of the lower critical limit value for a period of time that is longer than the established time delay by the measured minute volume.

23. A control device according to claim 22, wherein software is implemented on the control device for executing the measuring of the minute volume, for determining the median of the minute volume as well as the lower critical limit value of the minute volume, the alarm limit value and the one of the time delay, with which time delay an alarm is generated, after undershooting the lower critical limit value, and the maximum tolerated duration of apnea of the patient, for receiving the median of the minute volume, the lower critical limit value of the minute volume and the one of the time delay and the maximum tolerated duration of apnea in the control device, for determining the reference signal and for generating of the alarm signal and wherein any or all of the lower critical limit value of the minute volume, the time delay, the alarm limit value, and the maximum tolerated duration of apnea are output as current setting data via an output unit connected to the control device.

24. A device for monitoring a patient under machine-assisted ventilation, the device comprising:
an input unit;
an output unit;
an analysis unit; and
at least one data link for data transfer between the analysis unit and a ventilator, wherein:
the analysis unit receives values of a measured minute volume, that are fed to the analysis unit via the data link;
the analysis unit is configured to determine a median of the minute volume on the basis of the measured minute volume;
the input unit comprises a menu navigation which receives an input of a lower critical limit value of the minute volume and a time delay, with which an alarm signal, after undershooting the lower critical limit value for a period of the time delay, is generated;
the lower critical limit value of the minute volume and the time delay value are fed via the data link to the analysis unit;
at least one reference signal that is a time behavior of a filtered minute volume signal is determined in the analysis unit, the reference signal being based on the input lower critical limit value for the determined median of the minute volume and the input time delay setting based on the determined median of the minute volume, which reference signal determines an alarm limit value, located below the lower critical limit value, as well as a maximum tolerated duration of apnea of the patient; and
an optically and/or acoustically perceptible alarm signal is issued via the output unit during machine-assisted ventilation upon an undershooting of the lower critical limit value for a period of time which is longer than the established time delay by the measured minute volume and upon an undershooting of the alarm limit value by the measured minute volume.

25. A device in accordance with claim 24, wherein values for the lower critical limit value, the alarm limit value, the time delay and the maximum tolerated duration of apnea are recorded in hash tables in the analysis unit and/or in a data storage device connected to same.

26. A device in accordance with claim 24, wherein historical information about a past course of the minute volume and/or about values of the minute volume that were found below the lower critical limit value but above the alarm limit value can be filed away in the analysis unit and/or in a data storage device connected to same and can be displayed via the output unit.

27. A device in accordance with claim 24, wherein any or all of the lower critical limit value of the minute volume, the time delay, the alarm limit value, and the maximum tolerated duration of apnea are output as current alarm setting data via the output unit connected to the control device.

* * * * *